United States Patent [19]

Jin et al.

[11] Patent Number: 5,063,195

[45] Date of Patent: Nov. 5, 1991

[54] HIGH EFFICIENCY SILVER CATALYST FOR THE PRODUCTION OF ETHYLENE OXIDE VIA ETHYLENE OXIDATION

[75] Inventors: JiQuan Jin, Beijing; Lian Di Shang, Tianjin; Guo Quan Jin; Yong Xu, both of Beijing; Guo Chun Luo, Tianjin, all of China

[73] Assignees: China Petrochemical Corporation, Beijing, China; Beijing China Research Institute of Beijing Yanshan Petrochemical Corporation, Beijing, China

[21] Appl. No.: 304,531

[22] Filed: Feb. 1, 1989

[30] Foreign Application Priority Data

Feb. 3, 1988 [CN] China .............................. 88100400.6

[51] Int. Cl.$^5$ ....................... B01J 21/04; B01J 23/02; B01J 23/50
[52] U.S. Cl. ................................... 502/341; 502/348; 549/534; 549/537
[58] Field of Search ....................... 502/341, 347, 348; 423/628

[56] References Cited

U.S. PATENT DOCUMENTS

| 3,962,136 | 6/1976 | Nielsen et al. | 252/454 |
| 4,066,575 | 1/1979 | Winnick | 252/475 |
| 4,379,134 | 4/1983 | Weber et al. | 423/626 |
| 4,575,494 | 2/1984 | Young et al. | 502/348 X |
| 4,837,194 | 6/1989 | Hayden | 502/348 |

FOREIGN PATENT DOCUMENTS 1422451  1/1976  United Kingdom .

Primary Examiner—W. J. Shine
Attorney, Agent, or Firm—Armstrong, Nikaido, Marmelstein, Kubovcik & Murray

[57] ABSTRACT

A process for preparing silver-containing catalysts and their carriers for the production of ethylene oxide via ethylene oxidation and also to the applications of said catalysts in producing ethylene oxide.

Commercial trihydrated α-alumina, boehmite, carbonaceous materials, a fluxing agent, fluoride and a binder are mixed with water, kneaded and extruded to form strips which are cut and shaped. The shaped bodies are dried, calcined and converted to a α-alumina bodies i.e., carriers. This process is characterized by using trihydrated α-alumina, boehmite alumina and carbonaceous materials which have a good matching of particle sizes and proportions in preparing alumina carriers with the following pore structure:

| specific surface area | 0.2–2 m$^2$/g |
| pore volume | >0.5 ml/g |
| pore radius | >30μ, 25–10% of total volume |
|  | <30μ, 75–90% of total volume. |

The alumina carriers are impregnated with silver compounds and promoters, and then dried, activated and used in ethylene oxidation for making ethylene oxide. The selectivity of the catalyst reaches from 83 to 84 percent.

21 Claims, No Drawings

HIGH EFFICIENCY SILVER CATALYST FOR THE PRODUCTION OF ETHYLENE OXIDE VIA ETHYLENE OXIDATION

BACKGROUND OF THE INVENTION

This invention relates to a process of preparing silver-containing catalysts and their carriers for the production of ethylene oxide via ethylene oxidation, and to the use of such catalysts to produce ethylene oxide. Ethylene oxide is produced by ethylene oxidation, and carbon dioxide is also formed in a side reaction. The heat of the side reaction is twenty times that of the main reaction and if not removed in time the ethylene oxide produced in the reaction will be further oxidized to carbon dioxide. In order to increase the activity of the catalysts, the sufficient specific surface area of silver particles must be afforded. Therefore, the catalyst carriers are required to have enough specific surface area. However, oversized specific surface area will make the transfer of the reaction heat difficult, aggravate side reaction and decrease the selectivity of the catalysts. In order to offer the catalysts a high selectivity, an ideal pore structure which matches the surface of the catalyst is required so that suitable conditions for heat and mass transfer can be attained and the unwanted side reaction can be suppressed. Since the reaction takes place under nearly diffusion-controlling conditions, the search for carriers with an optimum matching between pore structure and specific surface area has become an important subject in developing silver catalysts having a high selectivity.

The alumina carriers prepared by the process disclosed in U.S. Pat. No. 4,379,134 have a specific surface area of less than one square meter per gram, generally, from 0.2 to 0.6. The volume fraction of the pores having the diameter of from 20 to 100 micrometer does not exceed 10 percent of the total pore volume. However, the alumina carriers prepared by the process of GB Pat. No. 1,465,523 have a wide range of the specific surface area from 0.1 to 60 square meter per gram, the fraction of the pores having the diameter of larger than 0.1 micrometer is only 40 percent of the total volume. The selectivity of the silver catalysts produced from said carriers is better than that of the silver catalysts produced from oversized the carriers having larger specific surface area, but is still not high.

The purpose of the invention is to avoid the disadvantages arising from oversized or undersized pore structure and specific surface area and inadequate pore-size distribution in the prior art. The present invention relates to alumina carriers having a better match between a specific surface area which compliments the pore structure of the and carrier greatly increases the selectivity of the silver catalysts in commercial applications.

SUMMARY OF THE INVENTION

The purpose of the invention can be reached by the following steps: trihydrated α-alumina, boehmite alumina and a carbonaceous materials which possesses a specific particle size distribution, are mixed with a fluxing agent, a fluoride, a binder and water in a mixer. The mixture is kneaded to form a extrudable paste. The extrudable paste is then extruded into strips which are cut to shaped bodies. The shaped bodies are then dried at a temperature of from 80° C. to 120° C. to reduce their water content below 25 percent, then calcined at a high temperature of from 1450° C. to 1550° C. in a tunner kiln, and converted to alpha-alumina carriers which have the following properties:

| Specific Surface Area | 0.2–2 m$^2$/gm, preferably 0.8–1.3 m$^2$/gm |
|---|---|
| Total Pore Volume | >0.5 ml/gm, preferably 0.5–0.7 ml/gm |
| Pore radius | % of total volume |
| <30μ | 75–90 |
| >30μ | 25–10 |

DETAILED DESCRIPTION OF THE INVENTION

Differing from the process disclosed in U.S. Pat. No. 4,379,134 in which all alumina starting materials used are expensive boehmite alumina, this invention uses cheaper commercial trihydrated α-alumina with less sodium as a part of the alumina starting materials. The amount of the cheaper alumina is from 50 to 90 percent of the alumina by weight. Moreover, according to the requirement of the pore formation, different particle sizes, trihydrated α-alumina of less than 50 mesh and boehmite alumina of less than 200 mesh, are chosen to provide the final alumina carriers with desired pore structure. Trihdrated α-alumina and boehmite alumina are mixed in proportions of from 1:1 to 9:1 based upon the weight of alumina.

The invention uses carbonaceous materials to make large pores. Said carbonaceous materials include petroleum coke, carbon powders, graphite, polyethylene and rosin and the mixture thereof. Carbonaceous materials are carbonated and oxidized and become escaping gas during calcination. In this way large pores are formed in the carriers, which benefit the diffusion and heat transfer of the reaction gases in the catalysts. Although U.S. Pat. No. 4,379,134 discloses the use of carbonaceous materials to make large pores with reference to U.S. Pat. Nos. 3,726,811 and 3,119,660, the fraction of the large pores having the diameter of greater than 20 μ accounts for only 5 percent of the total pore volume (less than 10%). The present invention shows that if the fraction of the large pores having the radius of greater than 30 μ is from 10 to 25 percent of the total pore volume, the selectivity of the catalyst will increase significantly. According to the invention, the particle size of carbonaceous materials is from 20 to 200 mesh and the amount of added carbonaceous materials ranges from 10 to 40 percent of the weight of the alumina, preferably 20–30% percent.

Fluxing agents can decrease the calcination temperature, make the alumina carriers have enough crush strength. Magnesium nitrate or magnesium oxide or feldspar can be selected as a fluxing agent in the invention. Their amount ranges from 1.0 to 7 percent of the alumina by weight. When the alumina carriers have an outside diameter of 6.5 mm, an inner diameter of 2.5 mm and a length of 6.5 mm, the crush strength of the alumina carriers is greater than 5 kg per particle.

Binders make crystal alumina disperse and bind during mixing to form an extrudable paste. The binders used in the invention include nitric acid, alumina gel, propanoic acid, acetic and formic acid. The amount of added nitric acids or alumina gel ranges from 25 to 60 percent of the alumina by weight.

Fluorides make alumina easy to transform into crystals and said alumina is converted completely into α-alumina crystals during the calcination, which benefits the elimination of unneccessary micropores. The fluorides used in the invention consist of ammonium fluoride, hydrogen fluoride and aluminium fluoride. The amount of the added fluoride anions accounts from 0.5 to 5.0 percent of the alumina by weight.

According to the present invention, after being extruded and shaped, the paste is dried to a water content of less than 30 percent. The carriers can take shapes of rings, balls, perforated cylinders. The carrier bodies are dried at 80° C. to 120° C. for a period of 1 to 24 hours, which is controlled according to the water content.

After being dried, said carrier bodies are heated to a temperature from 1450° C. to 1550° C. and kept at the temperature for about 2 to 6 hours so that all alumina are converted to α-alumina. Meanwhile, the fluoride anions can eliminate micropores to make the pores having the radius of less than 30 μ range from 0.5 μ to 5 μ and the pores having the radius of larger than 30 μ amount from 25 to 10 percent of the total volume.

Silver catalysts are prepared from alumina bodies by impregnating them with solutions of silver compounds. Promoters are impregnated simultaneously onto the alumina bodies as well as before or after the impregnation of the silver compounds or after the reduction of silver compounds to silver. The carriers are impregnated with a silver compound solution sufficient to allow the silver to be supported on the carrier in an amount of 1–25% of the weight of the catalyst, the impregnated carriers are then separated from the solution and the silver compound is reduced to silver and the silver impregnated carrier is activated.

Silver oxalate is precipitated by mixing aqueous solutions of silver nitrate and ammonium oxalate. The precipitate is then filtered and washed to eliminate nitrate anions. Said silver oxalate is then dissolved in an aqueous solution of ethyldiamine and diethanolamine and promoters are added to form an impregnation solution. The alumina carrier is impregnated with said impregnation solution and drained and heated in an air flow at a temperature from 550° C. to 600° C. for a duration to produce a silver catalyst containing 5 to 20 percent of silver by weight. Silver nitrate can also be replaced by silver oxide. Alternatively, silver oxalate can directly form a complex with amines without filtration and then the alumina carriers will be impregnated with the complex solution.

The promoters are usually impregnated onto the catalyst in amounts of from 20 to 1000 parts of alkali metals such as potassium, rubidium and cesium and less than 1000 parts of alkaline earth metals such as barium (calculted on metal) per million parts of the catalyst by weight. Cesium is preferably selected among aforesaid alkali metals. When or before or after said silver compound is supported on the carriers, in addition to the silver compound, one or more metals chosen from the alkali metals such as potassium, rubidium and cesium is or are supported on said carriers in a sufficient amount so that 40 to 1000 parts of the alkali metals (calculated on metals) are deposited on one million parts of the catalyst by weight.

The alkali metals deposited on the alumina carriers can be washed with absolute alcohol or absolute methanol. The concentration of the alkali metals can be controlled in a certain range, because some of the alkali metals are cleaned away.

The alumina carriers impregnated are heated in an air flow at a temperature of about 550° C. for a minute and the resulting silver catalyst contains 15 percent of silver, 200 ppm barrium and 600 ppm cesium.

Catalysts are evaluated with a single tube reactor with an inner diameter of 21 mm, a bed height of 7.07 m and an effective volume of 2.45 liter. There is a jacket outside the reactor tube through which a heat-conducting oil is passed to heat up the reactor or remove the heat of reaction. The conditions used in the evaluation are as follows:

Constitution of the reacting gases:

| | |
|---|---|
| $C_2H_4$ | 20% mole |
| $O_2$ | 7% mole |
| $CO_2$ | <8% mole |
| $N_2$ | rest |

Concentration of

| | |
|---|---|
| Ethylene oxide in the Effluent from the reactor | 1.3–1.4% mole |
| Reaction Pressure | 21 Kg/cm$^2$ |
| Space Velocity | 7000/h |
| Time-Space Yield | 180–200 g Ethylene Oxide/ 1 Cat. h | controlling the dichloroethane content of the reaction gas and making the selectivity of the catalyst the highest.

The selectivity of the catalysts prepared in the embodiments in the invention reaches 84.1% at a reaction temperature of 233° C.

All kinds of the silver catalysts prepared by the process of the invention are evaluated in a single tube reactor or micro reactor. The single tube reactor has a diameter of 21 mm, a 7.07 m height of the catalyst bed and an effective volume of 2.5 liter.

Constitution of the reacting Gas:

| | |
|---|---|
| $C_2H_4$ | 12–25% (mole concentrations) |
| $O_2$ | 6.5%–7.5% |
| $CO_2$ | 6–10% |
| $N_2$ | rest |
| Dichloroethane | 0.05–1.05 ppm |
| Space Velocity | 7000/hour |
| Temperature | 220–245° C. |
| Pressure | 21 Kg/cm$^2$ |
| Ethylene oxide in the Effluent | 1.3–1.6% |
| Time-Space Yield | 170–260 g Ethylene Oxide/l Cat. h |

The constitution of the inlet and exit gases of the reactor are measured continuously when the conditions described above are reached. The selectivity of the catalyst is calculated by the following equation after correcting the data for volume thrinkage.

$$\text{selectivity } S = \frac{\Delta EO}{\Delta EO + 0.5\Delta CO_2} \; 100\%$$

Wherein, $\Delta EO$ is the concentration difference of the ethylene oxide between exit and inlet gases.

Once the temperature remains unchanged (between 220° and 245° C.) with a constant conversion and the maximum selectity, the continous measurement is carried out again and the selectivity is calculated by averaging the data of more than 30 groups.

Compared with the prior art compositions, the present invention has the following advantage: the silver catalysts prepared by the process of the invention are particularly suitable for ethylene oxidization to produce ethylene oxide and has a selectivity of from 83 to 84 percent in the conditions disclosed above in industrial facilities.

The invention will be further described in detail in the following examples:

EXAMPLE 1

77 kilograms of trihydrated α-alumina of less than 50 mesh with low sodium content, 23 kilograms of boehmite alumina of less than 200 mesh, 1.7 kilograms of ammonium fluoride, 20 kilograms of petroleum coke of 30-200 mesh, 2 kilograms of magnesium nitrate were uniformly mixed in a mixer. 20 kilograms of said mixture were placed into a kneading machine, to which 2.7 liters of dilute nitric acid (acid:water=1:3) and an adequate amount of water were added. The mixture was kneaded to form an extrudable blend. Said extrudable blend was then extruded to become a ring shaped bodies having an outside diameter of 6.5 mm, a length of 6.5 mm and a inner diameter of 2.5 mm. Said ring shaped bodies were dried at a temperature of from about 80° C. to 100° C. for more than 2 hours to lower the water content of the bodies to below 25 percent and then calcined in a tunnel kiln, the temperature of which rised to 1480° C. in 6 hours and remained constant for 6 hours. After the temperature of the tunnel kiln went down, pure alumina ring shaped bodies were obtained which had physical properties as follows:

| Crush strength | kg/particle | 5.5 |
|---|---|---|
| Water absorption | % | 68 |
| Bulk Density | gm/cm$^3$ | 0.55 |
| Specific surface area | m$^2$/g | 1.1 |
| pore volume | ml/g | 0.56 |

| pore radius | distribution | <% of total volume> |
|---|---|---|
| <0.5 | μ | 12.8 |
| 0.5-1 | μ | 36.3 |
| 1-5 | μ | 23.0 |
| 5-10 | μ | 5.6 |
| 10-30 | μ | 5.8 |
| 30-51 | μ | 7.3 |
| >51 | μ | 9.2 |

A catalyst was prepared by the following steps: 2.8 kilograms of silver nitrate were dissolved into 3 liters of deionized water, 1.12 kilograms of ammonium oxalate were dissolved into 11 liters of deionized water at 50° C. Said two solutions were mixed and white silver oxalate was precipitated. Then the precipitate was filtered and washed with distilled water until the washings contained no nitrate anions. The filter cake contained about 50 percent of silver and about 30 percent of water.

1.2 kilograms of ethyldiamine, 0.4 kilograms of diethanolamine, 1.5 kilograms of deionized water were added into a container made of stainless steel with a stirror to get mixed solution. The filter cake of silver oxalate prepared were added into the mixed solution with stirring at below 40° C. to dissolve all silver oxalate. Then 4.5 grams of barium acetate, 9.5 grams of cesium sulfate and about 1 kilograms of deionized water were added into the above mixed solution to form an impregnation solution which had 22 percent of silver, 300 ppm of barium and 900 ppm of cesium.

3 kilograms of the carriers were placed into a container which can be evacuated to below 10 mmHg. Said impregnation solution was added, and the carrier was immersed for 30 minutes and then the extra solution was dripped away.

EXAMPLE 2

Alumina ring shaped bodies i.e. carriers were prepared by means of the procedure similar to Example 1 except that 32 kilograms of graphite power were substituted for petroleum coke and aluminium gel having about 10 percent of alumina was substituted for nitric acid for shaping. The alumina ring shaped bodies have physical properties as follows:

| Crush strength | kg/particle | 6.5 |
|---|---|---|
| Water absorption rate | % | 72.0 |
| Bulk Density | gm/cm$^3$ | 0.50 |
| Specific surface area | m$^2$/g | 1.1 |
| pore volume | ml/g | 0.66 |

| pore radius | distribution | <% of total volume> |
|---|---|---|
| <0.5 | μ | 7.3 |
| 0.5-1 | μ | 27.0 |
| 1-5 | μ | 35.0 |
| 5-10 | μ | 6.2 |
| 10-30 | μ | 1.6 |
| 30-51 | μ | 15.0 |
| >51 | μ | 7.9 |

A catalyst was prepared by means of the same procedure as in Example 1.

The catalyst was evaluated by a single tube in the same conditions as Example 1. The temperature of the reaction remains 235° C. and the selectivity of the catalyst is 83.9%.

EXAMPLE 4-8

Alumina ring shaped bodies and silver catalysts were prepared by the same procedure as Example 1. A variety of catalysts containing different amounts of barium was prepared through changing the barium content in the impregation solution. The catalysts were evaluated in microreactor with an inner diameter of 4 mm, a 8 cm height of the catalyst bed, an effective volume of 1 ml and catalyst sizes of from 11 to 18 mesh.

The reaction gas mixtures were prepared in advance by mixing the concerned gases in a high pressure cylinder. The constitution of the reaction gas and the conditions for the evaluation were the same as Example 1. Dichloroethane, a restrainer in the reaction gas had a content of 0.4 ppm. The reaction temperature and the selectivity were measured. The results were shown in Table 1.

TABLE 1

| Examples | Ba in Impregnation solution ppm | Ag in catalyst % | Ba in catalyst ppm | Evaluation Temperature °C. | Results ΔEO % | S % |
|---|---|---|---|---|---|---|
| 4 | 0 | 15.6 | 0 | 222 | 1.39 | 82.1 |
| 5 | 300 | 15.9 | 130 | 227 | 1.38 | 83.9 |
| 6 | 500 | 15.4 | 350 | 224 | 1.38 | 83.2 |
| 7 | 700 | 15.3 | 490 | 226 | 1.38 | 83.0 |
| 8 | 900 | 14.9 | 610 | 226 | 1.38 | 82.7 |

COMPARATIVE EXAMPLE 3

Alumina bodies were prepared with the same prescription as Example 2 and by the same method as Example 1 except that the amount of added graphite was 2/5 of the amount used in Example 2. The physical properties of the alumina bodies prepared were as follows:

| | | |
|---|---|---|
| Crush strength | kg/particle | 9.3 |
| Water absorption rate | % | 69.0 |
| Bulk Density | gm/cm$^3$ | 0.50 |
| Specific surface area | m$^2$/g | 1.06 |
| pore volume | ml/g | 0.63 |

| pore radius | distribution | <% of total volume> |
|---|---|---|
| <0.5 | μ | 8.5 |
| 0.5–1 | μ | 12.5 |
| 1–5 | μ | 68.0 |
| 5–10 | μ | 7.5 |
| 10–30 | μ | 0.2 |
| 30–51 | μ | 1.2 |
| >51 | μ | 1.8 |

A catalyst was prepared by the same method as Example 1.

The catalyst was evaluated in a single tube in the same conditions as Example 1. The reaction took place at a temperature of 237° C. The selectivity of the catalyst was 77.7 percent.

EXAMPLES 9–11

Catalysts and alumina bodies were prepared in the same way as Example 1 except that the cesium content in impregnation solutions was changed and the evaluation of the catalysts was done in the same way as Example 4–8. The results are shown in Table 2.

TABLE 2

| Examples | Cs in Impregnation solution ppm | Ag in catalyst % | Cs in catalyst ppm | Evaluation Temperature °C. | Results ΔEO % | S % |
|---|---|---|---|---|---|---|
| 9 | 500 | 12.3 | 280 | 231 | 1.39 | 83.3 |
| 10 | 700 | 12.7 | 400 | 236 | 1.39 | 84.4 |
| 11 | 900 | 13.3 | 540 | 243 | 1.37 | 83.9 |

While the invention has been described in connection with what is presently considered to be the most practical and preferred embodiments, it is understood that the invention is not to be limited to the disclosed embodiments, but on the contrary, is intended to cover various modifications and equivalent arrangements included within the spirit and scope of the appended claims.

We claim:

1. A process for preparing a silver-containing catalyst for the production of ethylene oxide via ethylene oxidation, comprising:

preparing a mixture of commercial trihydrated α-alumina, boehmite alumina, carbonaceous material, a fluxing agent, a fluoride, a binder and water;

extruding the mixture to form a shaped body;

drying and calcining the shaped body to convert it into an alumina carrier having the following pore structure:

| | |
|---|---|
| Specific surface area | 0.2–2 m$^2$/g |
| pore volume | >0.5 ml/g |
| pore radius | 10–25% of the total volume being greater than 30μ | impregnating the alumina carrier with a solution of a silver compound and an alkali or alkaline earth metal compound; and reducing and activating said silver impregnated carrier.

2. The process of claim 1, wherein said trihydrated α-alumina is commercial trihydrated α-alumina of low sodium content with a particle size of less than 50 mesh.

3. The process of claim 1, wherein said boehmite alumina is a boehmite alumina with a particle size of less than 200 mesh.

4. The process of claim 1, wherein said trihydrated α-alumina and boehmite alumina are mixed in proportions of from 1:1 to 9:1 based upon the weight of alumina.

5. The process of claim 1, wherein said carbonaceous material has a particle size of from 20 to 200 mesh and is selected from the group consisting of petroleum coke, carbon, graphite, polyethylene, rosin and mixtures thereof in an amount of from 10 to 40 percent of alumina by weight.

6. The process of claim 5, wherein said carbonaceous material is present in an amount of from 20 to 30 percent of alumina by weight.

7. The process of claim 1, wherein said fluxing agent is one agent selected from the group consisting of magnesium nitrate, magnesium oxide and feldspar.

8. The process of claim 7, wherein said fluxing agent is present in an amount of from 1 to 7 percent of alumina by weight.

9. The process of claim 1, wherein said fluoride is selected from the group consisting of aluminium fluoride, ammonium fluoride and hydrogen fluoride.

10. The process of claim 9, wherein said fluoride is present in an amount of from 0.5 to 5 percent of the weight of alumina calculated on fluoride anions.

11. The process of claim 1, wherein said binder is dilute nitric acid (HNO$_3$:H$_2$O=1:3) or alumina gel.

12. The process of claim 11, wherein said binder is present in an amount of from 25 to 60 percent of alumina by weight.

13. The process of claim 1, wherein said mixture of carrier component is extruded, cut and shaped into a ring, cylinder, ball or perforated cylinder shaped carrier.

14. The process of claim 1, wherein said calcining is done at from 1450° C. to 1550° C. for from 2 to 6 hours.

15. The process of claim 1, wherein said carrier is impregnated with a silver compound solution sufficient to allow the silver to be supported on the carrier in an amount of 1–25% of the weight of the catalyst, and further comprising separating the impregnated carrier from the solution prior to reducing the silver compound to silver.

16. The process of claim 1, wherein said carrier is impregnated with a promoter selected from the group consisting of alkali metal and alkaline earth metal compounds.

17. The process of claim 16, wherein the alkali metal compound is a compound containing potassium, rubidium or cesium and being supported on said carrier in an amount so that 40 to 1000 parts of alkali metal is deposited per one million parts of the catalyst by weight.

18. The process of claim 15, wherein the alkaline earth metal compound is supported on the catalyst as a promoter in an amount of less than 1000 parts per million parts of the catalyst by weight.

19. The process of claim 16, wherein said alkaline earth metal compound is barium acetate.

20. The process of claim 18, wherein barium acetate is supported in an amount of less than 1000 parts of barium per million parts of said catalyst by weight.

21. A silver-containing catalyst prepared by the process as claimed in claim 11.

* * * * *

UNITED STATES PATENT AND TRADEMARK OFFICE
CERTIFICATE OF CORRECTION

PATENT NO. : 5,063,195
DATED : November 5, 1991
INVENTOR(S) : JiQuan Jin, et al

It is certified that error appears in the above-indentified patent and that said Letters Patent is hereby corrected as shown below:

```
Column 8, line 57, "15" should read -- 16 --;
         line 67, "11" should read -- 1 --.
```

Signed and Sealed this

Eighth Day of June, 1993

Attest:

MICHAEL K. KIRK

*Attesting Officer*    Acting Commissioner of Patents and Trademarks